(12) United States Patent
Konstantino et al.

(10) Patent No.: US 11,529,500 B2
(45) Date of Patent: *Dec. 20, 2022

(54) DEVICE AND METHOD FOR COMPARTMENTAL VESSEL TREATMENT

(71) Applicant: TriReme Medical, LLC, Pleasanton, CA (US)

(72) Inventors: Eitan Konstantino, Orinda, CA (US); Tanhum Feld, Moshav Merhavya (IL)

(73) Assignee: TriReme Medical, LLC, Pleasanton, CA (US)

( * ) Notice: Subject to any disclaimer, the term of this patent is extended or adjusted under 35 U.S.C. 154(b) by 410 days.

This patent is subject to a terminal disclaimer.

(21) Appl. No.: 16/736,633

(22) Filed: Jan. 7, 2020

(65) Prior Publication Data

US 2020/0215311 A1 Jul. 9, 2020

Related U.S. Application Data

(63) Continuation of application No. 14/952,728, filed on Nov. 25, 2015, now Pat. No. 10,549,077, which is a continuation of application No. 13/044,425, filed on Mar. 9, 2011, now Pat. No. 9,199,066.

(60) Provisional application No. 61/313,600, filed on Mar. 12, 2010.

(51) Int. Cl.
*A61M 25/10* (2013.01)
*A61F 2/958* (2013.01)
*A61B 17/22* (2006.01)

(52) U.S. Cl.
CPC ........... *A61M 25/104* (2013.01); *A61B 17/22* (2013.01); *A61F 2/958* (2013.01); *A61B 2017/22001* (2013.01); *A61B 2017/22051* (2013.01); *A61M 2025/105* (2013.01); *A61M 2025/1084* (2013.01)

(58) Field of Classification Search
CPC .......... A61M 25/104; A61M 2025/105; A61M 2025/1084; A61B 17/22; A61B 2017/22001; A61B 2017/22051; A61F 2/958

See application file for complete search history.

(56) References Cited

U.S. PATENT DOCUMENTS

| 2,701,559 A | 2/1955 | Cooper |
| 2,854,983 A | 10/1958 | Baskin |
| 3,045,677 A | 7/1962 | Wallace |

(Continued)

FOREIGN PATENT DOCUMENTS

| CN | 1568165 A | 1/2005 |
| EP | 0 565 796 | 10/1993 |

(Continued)

OTHER PUBLICATIONS

AngioSculpt XL PT Scoring Balloon Catheter Brochure, AngioScore, Inc., Rev. C, May 2013.

(Continued)

*Primary Examiner* — Richard G Louis
(74) *Attorney, Agent, or Firm* — Knobbe, Martens, Olson & Bear, LLP

(57) ABSTRACT

An angioplasty balloon having an elastic constraining structure that partially expands with the balloon so that, at maximum balloon inflation, the constraining structure forms a pattern of channels or "pillows" on the balloon.

20 Claims, 6 Drawing Sheets

(56) References Cited

U.S. PATENT DOCUMENTS

| | | |
|---|---|---|
| 3,467,101 A | 9/1969 | Fogarty et al. |
| 3,825,013 A | 7/1974 | Craven |
| 4,327,736 A | 5/1982 | Inoue |
| 4,456,011 A | 6/1984 | Warnecke |
| 4,483,340 A | 11/1984 | Fogarty et al. |
| 4,637,396 A | 1/1987 | Cook |
| 4,723,549 A | 2/1988 | Wholey et al. |
| 4,796,629 A | 1/1989 | Grayzel |
| 4,921,484 A | 5/1990 | Hillstead |
| 4,976,711 A | 12/1990 | Parins et al. |
| 4,998,539 A | 3/1991 | Delsanti |
| 5,071,407 A | 12/1991 | Porter et al. |
| 5,100,386 A | 3/1992 | Inoue |
| 5,133,732 A | 7/1992 | Wilkor |
| 5,176,693 A | 1/1993 | Pannek |
| 5,181,911 A | 1/1993 | Shturman |
| 5,190,058 A | 3/1993 | Jones et al. |
| 5,196,024 A | 3/1993 | Barath |
| 5,222,971 A | 6/1993 | Willard et al. |
| 5,224,945 A | 7/1993 | Pannek, Jr. |
| 5,263,963 A | 11/1993 | Garrison et al. |
| 5,308,356 A | 5/1994 | Blackshear, Jr. et al. |
| 5,320,634 A | 6/1994 | Vigil et al. |
| 5,336,178 A | 8/1994 | Kaplan |
| 5,336,234 A | 8/1994 | Vigil et al. |
| 5,344,419 A | 9/1994 | Spears |
| 5,449,372 A | 9/1995 | Schmaltz et al. |
| 5,456,666 A | 10/1995 | Campbell et al. |
| 5,456,667 A | 10/1995 | Ham et al. |
| 5,460,607 A | 10/1995 | Miyata et al. |
| 5,484,411 A | 1/1996 | Inderbitzen et al. |
| 5,501,694 A | 3/1996 | Ressemann et al. |
| 5,527,282 A | 6/1996 | Segal |
| 5,556,408 A | 9/1996 | Farhat |
| 5,562,620 A | 10/1996 | Klein et al. |
| 5,571,086 A | 11/1996 | Kaplan et al. |
| 5,607,442 A | 3/1997 | Fischell et al. |
| 5,609,574 A | 3/1997 | Kaplan et al. |
| 5,616,149 A | 4/1997 | Barath |
| 5,620,457 A | 4/1997 | Pinchasik et al. |
| 5,628,746 A | 5/1997 | Clayman |
| 5,628,755 A | 5/1997 | Heller et al. |
| 5,643,210 A | 7/1997 | Iacob |
| 5,643,312 A | 7/1997 | Fischell et al. |
| 5,695,469 A | 12/1997 | Segal |
| 5,702,410 A | 12/1997 | Klunder et al. |
| 5,713,863 A | 2/1998 | Vigil et al. |
| 5,730,698 A | 3/1998 | Fischell et al. |
| 5,733,303 A | 3/1998 | Israel et al. |
| 5,735,816 A | 4/1998 | Lieber et al. |
| 5,755,781 A | 5/1998 | Jayaraman |
| 5,772,681 A | 6/1998 | Leoni |
| 5,776,181 A | 7/1998 | Lee et al. |
| 5,797,935 A | 8/1998 | Barath |
| 5,810,767 A | 9/1998 | Klein |
| 5,827,321 A | 10/1998 | Roubin et al. |
| 5,863,284 A | 1/1999 | Klein |
| 5,868,708 A | 2/1999 | Hart et al. |
| 5,868,719 A | 2/1999 | Tsukernik |
| 5,868,779 A | 2/1999 | Ruiz |
| 5,868,783 A | 2/1999 | Tower |
| 5,869,284 A | 2/1999 | Cao et al. |
| 5,904,679 A | 5/1999 | Clayman |
| 5,906,639 A | 5/1999 | Rudnick et al. |
| 5,919,200 A | 7/1999 | Stambaugh et al. |
| 5,961,490 A | 10/1999 | Adams |
| 5,967,984 A | 10/1999 | Chu et al. |
| 5,987,661 A | 11/1999 | Peterson |
| 6,013,055 A | 1/2000 | Bampos et al. |
| 6,036,689 A | 3/2000 | Tu et al. |
| 6,036,708 A | 3/2000 | Sciver |
| 6,053,913 A | 4/2000 | Tu et al. |
| 6,059,810 A | 5/2000 | Brown et al. |
| 6,059,811 A | 5/2000 | Pinchasik et al. |
| 6,077,298 A | 6/2000 | Tu et al. |
| 6,102,904 A | 8/2000 | Vigil et al. |
| 6,106,548 A | 8/2000 | Roubin et al. |
| 6,129,706 A | 10/2000 | Janacek |
| 6,156,265 A | 12/2000 | Sugimoto |
| 6,190,403 B1 | 2/2001 | Fischell et al. |
| 6,206,910 B1 | 3/2001 | Berry et al. |
| 6,217,608 B1 | 4/2001 | Penn et al. |
| 6,235,043 B1 | 5/2001 | Reiley et al. |
| 6,241,762 B1 | 6/2001 | Shanley |
| 6,245,040 B1 | 6/2001 | Inderbitzen et al. |
| 6,258,099 B1 | 7/2001 | Mareiro et al. |
| 6,261,319 B1 | 7/2001 | Kveen et al. |
| 6,309,414 B1 | 10/2001 | Rolando et al. |
| 6,319,251 B1 | 11/2001 | Tu et al. |
| 6,334,871 B1 | 1/2002 | Dor et al. |
| 6,361,545 B1 | 3/2002 | Macoviak et al. |
| 6,416,539 B1 | 7/2002 | Hassdenteufel |
| 6,454,775 B1 | 9/2002 | Demarais et al. |
| 6,540,722 B1 | 4/2003 | Boyle et al. |
| 6,605,107 B1 | 8/2003 | Klein |
| 6,616,678 B2 | 9/2003 | Nishtala et al. |
| 6,626,861 B1 | 9/2003 | Hart et al. |
| 6,652,548 B2 | 11/2003 | Evans et al. |
| 6,656,351 B2 | 12/2003 | Boyle |
| 6,695,813 B1 | 2/2004 | Boyle et al. |
| 6,702,834 B1 | 3/2004 | Boylan et al. |
| 6,939,320 B2 | 9/2005 | Lennox |
| 6,942,680 B2 | 9/2005 | Grayzel et al. |
| 7,156,869 B1 | 1/2007 | Pacetti |
| 7,186,237 B2 | 3/2007 | Meyer et al. |
| 7,357,813 B2 | 4/2008 | Burgermeister |
| 7,686,824 B2 | 3/2010 | Konstantino et al. |
| 7,691,119 B2 | 4/2010 | Farnan |
| 7,708,748 B2 | 5/2010 | Weisenburgh, II et al. |
| 7,753,907 B2 | 7/2010 | DiMatteo et al. |
| 7,803,149 B2 | 9/2010 | Bates et al. |
| 7,931,663 B2 | 4/2011 | Farnan et al. |
| 8,172,793 B2 | 5/2012 | Bates et al. |
| 8,257,305 B2 | 9/2012 | Speck et al. |
| 8,348,987 B2 | 1/2013 | Eaton |
| 8,388,573 B1 | 3/2013 | Cox |
| 8,439,868 B2 | 5/2013 | Speck et al. |
| 9,179,936 B2 | 11/2015 | Feld et al. |
| 9,199,066 B2 * | 12/2015 | Konstantino ............ A61F 2/958 |
| 9,216,033 B2 | 12/2015 | Feld et al. |
| 9,375,328 B2 | 6/2016 | Farnan |
| 9,415,140 B2 | 8/2016 | Speck |
| 9,649,476 B2 | 5/2017 | Speck et al. |
| 10,220,193 B2 | 3/2019 | Feld et al. |
| 10,232,148 B2 | 3/2019 | Konstantino et al. |
| 10,524,825 B2 | 1/2020 | Feld et al. |
| 10,549,077 B2 * | 2/2020 | Konstantino ....... A61M 25/104 |
| 11,000,680 B2 | 5/2021 | Konstantino et al. |
| 11,234,843 B2 | 2/2022 | Feld et al. |
| 2002/0010489 A1 | 1/2002 | Grayzel et al. |
| 2003/0023200 A1 | 1/2003 | Barbut et al. |
| 2003/0040790 A1 | 2/2003 | Furst |
| 2003/0065354 A1 | 4/2003 | Boyle |
| 2003/0078606 A1 | 4/2003 | Lafontaine et al. |
| 2003/0114915 A1 | 6/2003 | Mareiro et al. |
| 2003/0114921 A1 | 6/2003 | Yoon |
| 2003/0120303 A1 | 6/2003 | Boyle et al. |
| 2003/0144726 A1 | 7/2003 | Majercak et al. |
| 2003/0153870 A1 | 8/2003 | Meyer et al. |
| 2003/0195609 A1 | 10/2003 | Berenstein et al. |
| 2003/0212449 A1 | 11/2003 | Cox |
| 2004/0034384 A1 | 2/2004 | Fukaya |
| 2004/0073284 A1 | 4/2004 | Bates et al. |
| 2004/0111108 A1 | 6/2004 | Farnan |
| 2004/0143287 A1 | 7/2004 | Konstantino et al. |
| 2004/0210235 A1 | 10/2004 | Deshmukh |
| 2004/0210299 A1 | 10/2004 | Rogers et al. |
| 2004/0230293 A1 | 11/2004 | Yip et al. |
| 2005/0021071 A1 | 1/2005 | Konstantino et al. |
| 2005/0021130 A1 | 1/2005 | Kveen et al. |
| 2005/0049677 A1 | 3/2005 | Farnan |
| 2005/0125053 A1 | 6/2005 | Yachia et al. |
| 2005/0271844 A1 | 12/2005 | Mapes et al. |
| 2006/0008606 A1 | 1/2006 | Horn et al. |

(56) References Cited

U.S. PATENT DOCUMENTS

| | | |
|---|---|---|
| 2006/0015133 A1 | 1/2006 | Grayzel et al. |
| 2006/0085025 A1 | 4/2006 | Farnan et al. |
| 2006/0085058 A1 | 4/2006 | Rosenthal et al. |
| 2006/0149308 A1 | 7/2006 | Melsheimer et al. |
| 2006/0259005 A1 | 11/2006 | Konstantino et al. |
| 2006/0271093 A1 | 11/2006 | Holman et al. |
| 2007/0073376 A1 | 3/2007 | Krolik et al. |
| 2007/0173923 A1 | 7/2007 | Savage et al. |
| 2008/0255508 A1 | 10/2008 | Wang |
| 2009/0036964 A1 | 2/2009 | Heringes et al. |
| 2009/0038752 A1 | 2/2009 | Weng et al. |
| 2009/0105686 A1 | 4/2009 | Snow et al. |
| 2009/0192453 A1 | 7/2009 | Wesselman |
| 2009/0227949 A1 | 9/2009 | Knapp et al. |
| 2009/0240270 A1 | 9/2009 | Schneider et al. |
| 2009/0319023 A1 | 12/2009 | Hildebrand et al. |
| 2010/0042121 A1 | 2/2010 | Schnieder et al. |
| 2010/0234875 A1 | 9/2010 | Allex et al. |
| 2010/0241215 A1 | 9/2010 | Hansen et al. |
| 2010/0331809 A1 | 12/2010 | Sandhu et al. |
| 2011/0066225 A1 | 3/2011 | Trollsas et al. |
| 2011/0071616 A1 | 3/2011 | Clarke et al. |
| 2011/0152905 A1 | 6/2011 | Eaton |
| 2011/0172698 A1 | 7/2011 | Davies et al. |
| 2012/0059401 A1 | 3/2012 | Konstantino et al. |
| 2012/0083733 A1 | 4/2012 | Chappa |
| 2012/0245607 A1 | 9/2012 | Gershony et al. |
| 2013/0046237 A1 | 2/2013 | Speck et al. |
| 2013/0116655 A1 | 5/2013 | Bacino et al. |
| 2013/0190725 A1 | 7/2013 | Pacetti et al. |
| 2013/0211381 A1 | 8/2013 | Feld |
| 2014/0276406 A1 | 9/2014 | Campbell et al. |
| 2015/0209556 A1 | 7/2015 | Timothy |
| 2016/0100964 A1 | 4/2016 | Feld et al. |
| 2019/0151627 A1 | 5/2019 | Konstantino et al. |
| 2019/0151631 A1 | 5/2019 | Feld et al. |
| 2020/0139093 A1 | 5/2020 | Feld et al. |
| 2021/0128891 A1 | 5/2021 | Konstantino et al. |
| 2021/0402160 A1 | 12/2021 | Konstantino et al. |
| 2022/0168120 A1 | 6/2022 | Feld et al. |

FOREIGN PATENT DOCUMENTS

| | | |
|---|---|---|
| EP | 0 623 315 | 11/1994 |
| EP | 0 832 608 | 4/1998 |
| EP | 1 042 997 | 10/2000 |
| EP | 2 035 291 | 3/2009 |
| JP | 2005-508709 | 4/2005 |
| JP | 2014-528809 W | 10/2014 |
| WO | WO 98/05377 | 2/1998 |
| WO | WO 98/50101 | 11/1998 |
| WO | WO 00/57815 | 10/2000 |
| WO | WO 2002/068011 | 9/2002 |
| WO | WO 2003/041760 | 5/2003 |
| WO | WO 2005/020855 | 3/2005 |
| WO | WO 2011/112863 | 9/2011 |
| WO | WO 2013/066566 | 5/2013 |
| WO | WO 2013/114201 | 8/2013 |
| WO | WO 2013/119735 | 8/2013 |

OTHER PUBLICATIONS

Bearing Works, (PTFE) Polytetrafluoroethylene material specifications sheet, available online Feb. 11, 2018 at https://www.bearingworks.com/uploaded-assets/pdfs/retainers/ptfe-datasheet.pdf; printed Feb. 21, 2018, in 2 pages.

Brydson, J.A., "Plastics Materials—Sixth Edition," 1995, p. 510, available in part online from https://books.google.com/books?id=wmohBQAAQBAJ&lpg=PA510&ots=G_4Q-OMpB4&dq=young's%20modulus%20of%20PEBAx&pg=PA510#v=onepage&q=young's%20modulus%20of%20PEBAx&f=false; printed on May 5, 2017.

Kadish, A., et al. "Mapping of Atrial Activation With a Noncontact, Multielectrode Catheter in Dogs," *Circulation: Journal of the American Heart Association*, (Apr. 1999) 99: 1906-1913.

International Search Report for Appl. No. PCT/US2011/027982 dated May 6, 2011 in 3 pages.

"Materials Data Book," Cambridge University Engineering Department, 2003, pp. 1-41.

\* cited by examiner

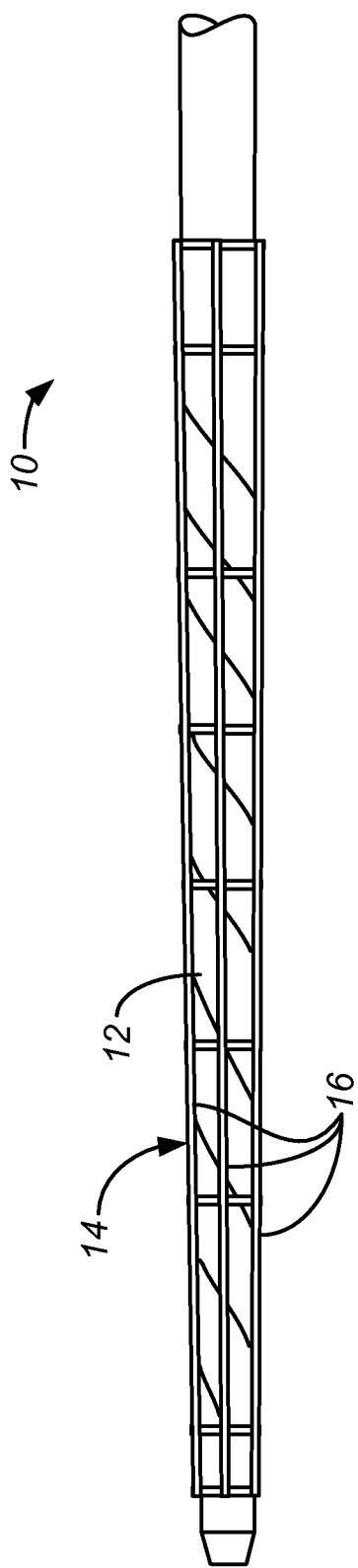
FIG. 2B1
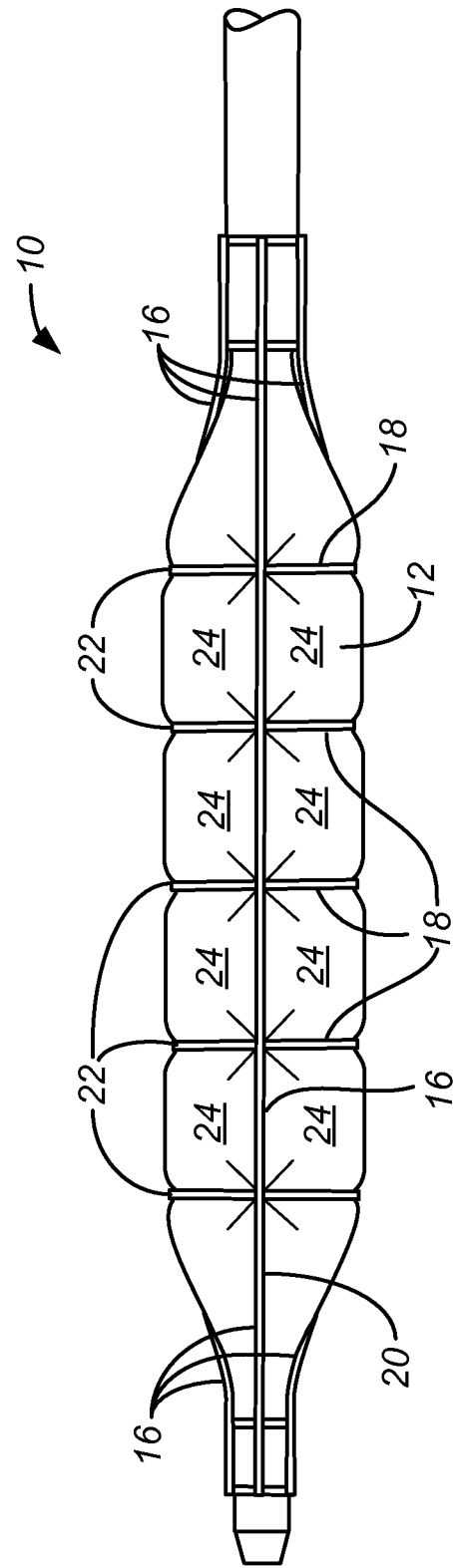
FIG. 2B2

DEVICE AND METHOD FOR COMPARTMENTAL VESSEL TREATMENT

This application claims the benefit of Provisional Application No. 61/313,600, filed on Mar. 12, 2010, the full disclosure of which is incorporated herein by reference.

BACKGROUND OF THE INVENTION

1. Field of the Invention

The present invention relates to the field of medical methods and devices, more specifically to medical angioplasty balloon catheters and devices intended to deliver active substances to body tissue.

Angioplasty balloons are one of the most commonly used tools for the treatment of narrowed blood vessels. These balloons are typically cylindrical when inflated and have different lengths and diameters to conform to different vessel sizes. The balloons are located at the distal end of flexible catheters and delivered to a target site/lesion where they are inflated at high pressure, normally between 8-20 atmospheres, in order to overcome the resistance of the lesion and achieve luminal expansion. Such high pressure angioplasty is often associated with trauma to the vessel walls with a resulting high frequency of vessel dissection (30%-40%), abrupt closure of the treated vessel (5%-12%), and restenosis. Thus, when conventional angioplasty is used as a primary treatment for occluded vessels, restenosis can occur in about 50% of the cases. Therefore, in the vast majority of coronary treatments, angioplasty is used as an initial treatment followed by placement of a stents. Frequently, the stents are coated with drug and polymer requiring the patient to take anti platelet therapy for extended periods, possibly lifelong, to limit the risk of stent thrombosis or blood clots. Anti platelet therapy increases the risk of bleeding and is expensive. In addition, patient must stop the antiplatelet therapy before any surgical intervention, thus increasing the risk of sudden death and often precluding beneficial procedures.

Dissections in blood vessels treated by balloon angioplasty are very common. The dissection rate is estimated to be as high as 30% of all cases. Some of the dissections are severe and may require urgent surgery or placement of additional stents. In addition, dissection may contribute to poor long term clinical results and restenosis even if a stent is placed in the treated lesion. Dissections are usually attributed to several mechanisms occurring during balloon inflation including shear forces applied on the vessel walls as the balloon pleats unfold as well as the uneven balloon inflation which occurs as a result of the non-symmetric nature of the vascular disease. During inflation, the balloon diameter increases in the radial direction as the folded balloon unwraps. As the folded lobes of the balloon open, the layers slide over one another and apply tangential forces to the lesion and/or vessel wall which can abrade the lesion or vascular wall and in the worst instances cause dissections. As shown in FIGS. 1A-1C, a catheter 10 is initially located in a region of plaque (P) in a blood vessel (BV). A balloon 12 on the catheter 10 has folded lobes which unfold as the balloon is inflated, as shown in FIG. 1B. The layers of the folded lobes move in opposite directions, as shown by the arrows in FIG. 1B, with the upper exposed layer tending to slide across the surface of the lesion or if present, exposed vascular wall. Such unintended lateral movement of the balloon surface can occur until the balloon is fully inflated, as shown in FIG. 1C.

Uneven inflation results from the uneven nature of the disease in the vessel. Angioplasty balloons are commonly non-compliant or semi-compliant, and when semi-compliant balloons are inflated against an eccentric lesion, the balloon will follow the "path of least resistance" and its diameter will increase more in the less diseased sections of the vessel, often increasing trauma in these areas.

For these reasons, it would be desirable to provide improved balloons and inflation structures for angioplasty balloons used in vascular treatments. In particular, it would be desirable to provide angioplasty balloons having a reduced tendency to cause trauma and dissection in the blood vessel walls as the balloon is inflated by modulating the inflation characteristics of the balloon and provide a segmented compartmental dilatation with local areas of compliance. It would be further desirable if the reduced dissections could also reduce the risk of elastic recoil and abrupt reclosure which are associated with current angioplasty balloons and their use. It would be further desired if such improved angioplasty balloon structures were compatible with each of stents, drug-eluting stents, and drug coated balloons. These advantages would preferably be obtained without loss of the ability of the catheters to increase the luminal size and restore blood vessel in the patient being treated. At least some of these objectives will be met by the invention as described hereinafter.

2. Description of the Background Art

U.S. Pat. Nos. 6,245,040 and 5,735,816, show balloon catheters having elastic spiral restraints which form spiral indentations in the balloon when inflated. Other patents of interest include U.S. Pat. Nos. 7,708,748; 7,686,824; 5,863,284; 5,772,681; 5,643,210; and 5,987,661.

BRIEF SUMMARY OF THE INVENTION

The present invention comprises a device for angioplasty or dilatation of stenotic vessels and optionally for the delivery of active substance to the vessel walls. A balloon catheter is designed to modulate the inflation characteristics of the balloon to provide a segmented compartmental dilatation with local regions of compliance capable of conforming to the uneven nature of the vascular disease. The balloon catheter of the present invention includes a constraining structure (CS) located over a balloon on a distal end of the catheter. The CS serves to control and limit balloon inflation and modify balloon topography, typically by forming protruding regions ("pillows") over the surface that cause local dilatation in a small region of the vessel independent of those formed by neighboring protruding regions. Such discrete protruding regions will each separately engage a segment of the lesion when the balloon is inflated so that the pressure and degree of balloon expansion applied against that segment is controlled and limited, thus reducing the risk of trauma while assuring that all segments of the lesion are adequately treated. The lesion can be uniformly treated along its length while excessive pressure against any one segment of the lesion can be reduced or avoided entirely. Such local dilatation avoids the "path of least resistance" phenomenon described above and allows local and non-uniform treatment for different sections or regions of the vessel, where the modified balloon topography minimizes trauma and injury of vessel wall as the balloon is inflated to the very high pressures associated with angioplasty. The CS also inhibits transfer of shear forces to the lesion and vessel wall as the balloon inflates and the wall layers open and slide laterally relative to the vessel wall. Conventional balloons present a continuous surface across the treated section of the vessel (sometimes as long as 200 mm to 300 mm in peripheral lesions) that leads to balloon deformation and uneven along the treated segment. Such an "aggregated dilatation" mechanism when applied to a diseased vessel having an uneven lesion geometry increases the probability of trauma and dissection. In contrast, the balloon of this invention provides for a more localized but balanced force distribution (e.g., as a result of the uniformly distributed protruding regions) along the length of the disease even when the disease varies significantly in size over its length.

In one embodiment of this invention, the CS is situated over the deflated and folded balloon and attached to a shaft of the catheter near a distal end of the balloon, near a proximal end of the balloon, or preferably both. The CS does not have to be attached to the balloon and can float over the folded balloon optionally having elastic covers at either or both ends (e.g., covers made of polymer). Upon balloon inflation, the CS expands to its maximum diameter and allows the balloon to further inflate through openings in the CS in a preselected pattern. Upon device deflation, the CS will elastically close to its original diameter.

In one embodiment of the invention as the balloon inflates, both the balloon and CS increase in diameter. The CS maximal open diameter, however, is smaller than fully inflated balloon diameter thus balloon continues to expand through the openings in the CS creating a series of protruding regions, typically in an orthogonal or diamond "quilted" pattern. The CS has a relatively small diameter before expansion and is capable of expanding due to inflation force applied by balloon expansion to a diameter smaller than that of the fully inflated balloon. The CS expansion is limited by its geometrical design.

The CS is designed to control balloon inflation by limiting and restricting balloon diameter across the treated segment in a way that will eliminate large diameter differences during the inflation process. Thus, when balloon pressure is increased, as is commonly done in order to overcome local narrowing, overstretching other parts of the treated lesion can be reduced or avoided entirely In addition, the CS can reduce or eliminate the transfer of tangential forces resulting from unfolding of the balloon against the vessel wall. The CS creates a network of crossing channels with protruding regions or "pillows" therebetween. The channels between the protruding regions prevent high radial stress buildup by providing stress relief regions between adjacent protruding regions. The stress relief regions can stretch or expand without being subjected to direct balloon surface contact thus minimizing trauma caused to vessel walls during inflation. In addition, the channels allow for plaque extrusion (redistribution) thus adding a new mechanism in addition to simple compression mechanism of conventional balloons.

In a first aspect, the present invention provides a system for performing angioplasty. The system includes a catheter shaft having an inflatable balloon at its distal end and a constraining structure disposed over the inflatable balloon. The constraining structure has a non-expanded configuration where it lies closely over or within folds of the balloon prior to inflation and an expanded configuration which is smaller than an unconstrained size of the balloon (when fully inflated) so that the structure restrains the balloon inflation along a plurality of crossing channel lines. By "crossing" channel lines, it is meant that the channels will intersect at a plurality of locations so that the channels comprise an intersecting matrix of interconnected channels. Individual channel lines may be oriented axially, circumferentially, or preferably will include channel lines with both axial and circumferential orientations where the axial channels intersect the circumferential channels. Alternatively, the channels could be formed as two or more counter wound helical channels that intersect to form diamond-shaped protruding regions.

In specific preferred embodiments, the constraining structure will comprise a plurality of circumferentially spaced-apart axial struts and a multiplicity of axially spaced-apart radially expandable rings attached to the axial struts. The rings are joined to the struts at intersecting angles, preferably in the range from about 75° to 105°. In particularly preferred embodiments, the intersecting angles will be 90°. The axial struts will be coupled to the catheter on both a distal side of the balloon and on a proximal side of the balloon. In some embodiments, at least one of the distal strut ends and the proximal strut ends will be free to translate axially over the catheter shaft as the balloon is inflated (to accommodate foreshortening which would otherwise occur). Alternatively, the individual struts may be fixedly attached to the catheter shaft on both the proximal and distal side of the balloon where the struts are elastic or otherwise stretchable in tension so that they will elongate as the balloon is inflated. For example, axial struts could be composed of an elastomer or other elastic material which allows elongation. More typically, the axial struts would include features, such as zig-zags, S-shaped links, coil springs, or the like, which would accommodate elongation (if needed) when either or both of the strut ends are attached to the catheter shaft.

The radially expandable rings will also be formed so that they can stretch or elongate to increase in diameter as the balloon is inflated in the ring. The expandable rings could be formed from inherently elastic materials, such as stretchable polymers or the like, but more typically will be formed with expansible features which allow the ring to expand when the balloon is inflated. The expandable features can be the same as with the axial struts, including zig-zags, S-shaped curves, coils, and the like. In all cases, it is necessary that the rings have an maximum diameter beyond which they will not further increase in size as the balloon is inflated. When the rings are formed with expandable features, the maximum ring expansion will occur when these features are fully elongated. If an elastomeric or other material is used to form the rings, non-distensible tethers or other expansion limits can be built into the rings so that they do not exceed their desired maximum diameter.

The balloons may also be coated or otherwise adapted to deliver drugs. Techniques for coating balloons with drugs are well described in the patent literature. See, for example, U.S. Pat. No. 7,750,041; US2010/02280228; US2010/0278744; and US2008/0102034, the full disclosures of which are incorporated herein by reference.

In a second aspect, the present invention provides a method for treating a lesion in a blood vessel. The method comprises inflating a balloon within the blood vessel where the balloon is constrained along a plurality of crossing channel lines, typically axial and/or circumferential channel lines which intersect and cross each other. The channel lines create a number of isolated protruding regions in the balloon, where the protruding regions contact the lesion while the channel lines are recessed away from the vessel wall. "Recessed" means that the bottom or trough of the channel line will be positioned radially closer to the axis of the catheter than is the inflated surface of the balloon. In many cases, the bottoms of the channels will not contact the lesion or blood vessel wall. In other cases, however, particularly when the plaque or thrombosis being extruded, the channels may fill with the lesion material while providing the benefits of stress relief described above since the bottoms of the channels will remain spaced radially inwardly from the blood vessel wall.

The balloon will typically be composed of a non-distensible or semi-compliant material so that it may be inflated at relatively high pressures, typically in the range from 10 atmospheres to 25 atmospheres, without over expanding within the blood vessel. Thus, both the balloon (when non-distensible) and the constraining structure will have maximum diameters when the balloon is fully inflated where the difference in the maximum diameters defines the depth of the channels which are formed in the balloon surface. The protruding regions will often have similar sizes (±50% of area engaging the lesion) and will be uniformly distributed over the balloon surface. The balloons may be used for angioplasty, without subsequent stent delivery and/or drug delivery. Alternatively, the balloons may be used for expanding a stent, including both drug-coated stents and uncoated stents. Finally, the balloons may themselves be coated with drug in order to transfer drug to the lesion or vessel wall during the treatment.

BRIEF DESCRIPTION OF THE DRAWINGS

FIGS. 2A, 2B1 and 2B2 show a constraining structure located on a balloon prior to inflation (FIG. 2B1) and after inflation (FIGS. 2A and 2B2).

DETAILED DESCRIPTION OF THE INVENTION

Figure 1A:
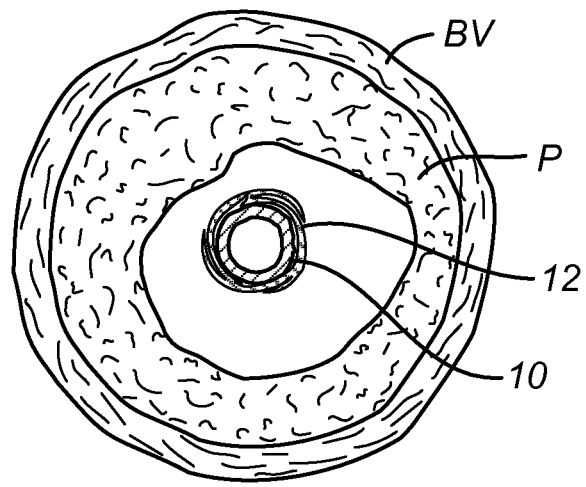
FIGS. 1A to 1C show a cross-section of the stages of unwrapping of conventional balloon inflation in a stenotic blood vessel.

The present invention provides a device for treating of diseased, blocked, occluded or stenotic lumens in the body, typically blood vessels including both arteries and veins, and more typically coronary and peripheral arteries. This device dilates occluded vessels while minimizing trauma to the lesion and luminal wall and reducing the risk of vessel trauma and injury. By placing an "elastic" constraining structure (CS) over a balloon of a balloon catheter, inflation of the balloon is controlled during balloon inflation and refolding of the balloon is aided as the balloon is deflated. The CS is designed to expand to a diameter smaller than the maximal diameter of the balloon when fully inflated. The CS structure applies radial resistance to inflation and is thus able to constrain the balloon and distribute or buffer the internal high pressure applied by the balloon to the luminal wall thus providing a controlled and less traumatic dilation process. The balloon which is typically formed from a non-distensible material such as a polyamide or a polyether block amide, will preferably be non-distensible or semi-compliant with a stretchability below 10% within typical inflation pressure ranges and a fully inflated size sufficiently large so that regions protrude through passages in the CS to form protruding regions which engage and dilate the lesion.

The CS can be coupled or otherwise connected to the catheter shaft on the distal side and/or the proximal side of the balloon. Alternatively, the CS can float over the balloon without fixed attachment using simple covers or constraints, and the CS is preferably designed to maintain its length during expansion of the balloon to limit relative axial movement between the CS and the balloon. The CS can be fabricated from various materials using suitable processes and designs. The CS can be made from metal, preferably an elastic metal such as a nickel-titanium alloy (Nitinol®) and/or from a variety of polymers (e.g., Nylon). For example, the CS can be constructed from wires or can be laser cut from a tube, sheath or other forms of materials.

In a preferred embodiment of this invention, the CS structure is located on the balloon and is expanded during balloon inflation. The CS expands to a smaller diameter than the balloon thus constricting balloon inflation within a cylindrical cage. Parts of the balloon, however, keep expanding through openings in the case of the CS creating controlled dilatation pattern and reducing or eliminating shear forces.

Once the CS reaches its maximum diameter (which is smaller than the maximum inflated balloon diameter), the balloon continues to inflate through openings in the CS creating a topography of protruding regions (hills) and channels (valleys) at the surface of the device, where the pattern of channels is defined by the geometry of the CS. The CS contributes to a controlled dilation process avoiding over expansion and minimizing the shear forces and uniform high pressure applied on the vessel wall as will be described in greater detail below with reference to FIGS. 6A-6C and 7.

Figure 1B:
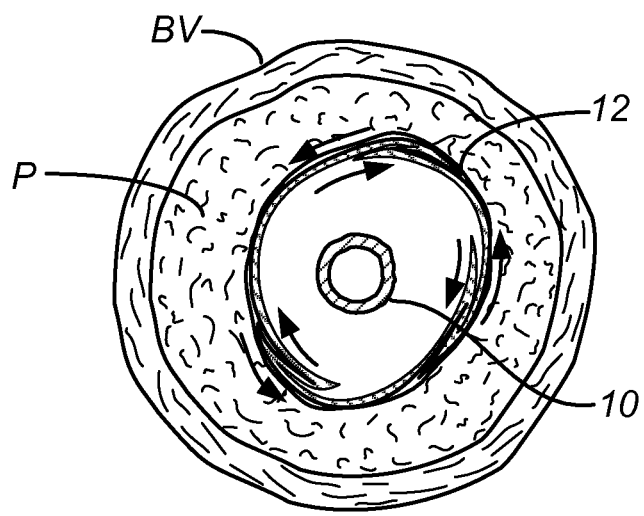
Figure 1C:
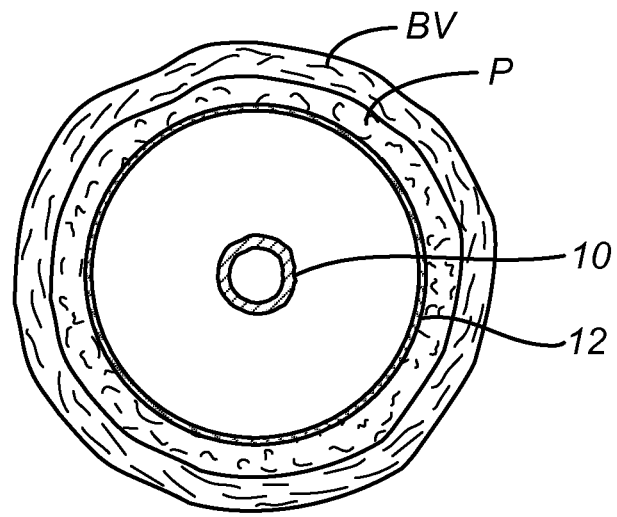
Figure 2A:
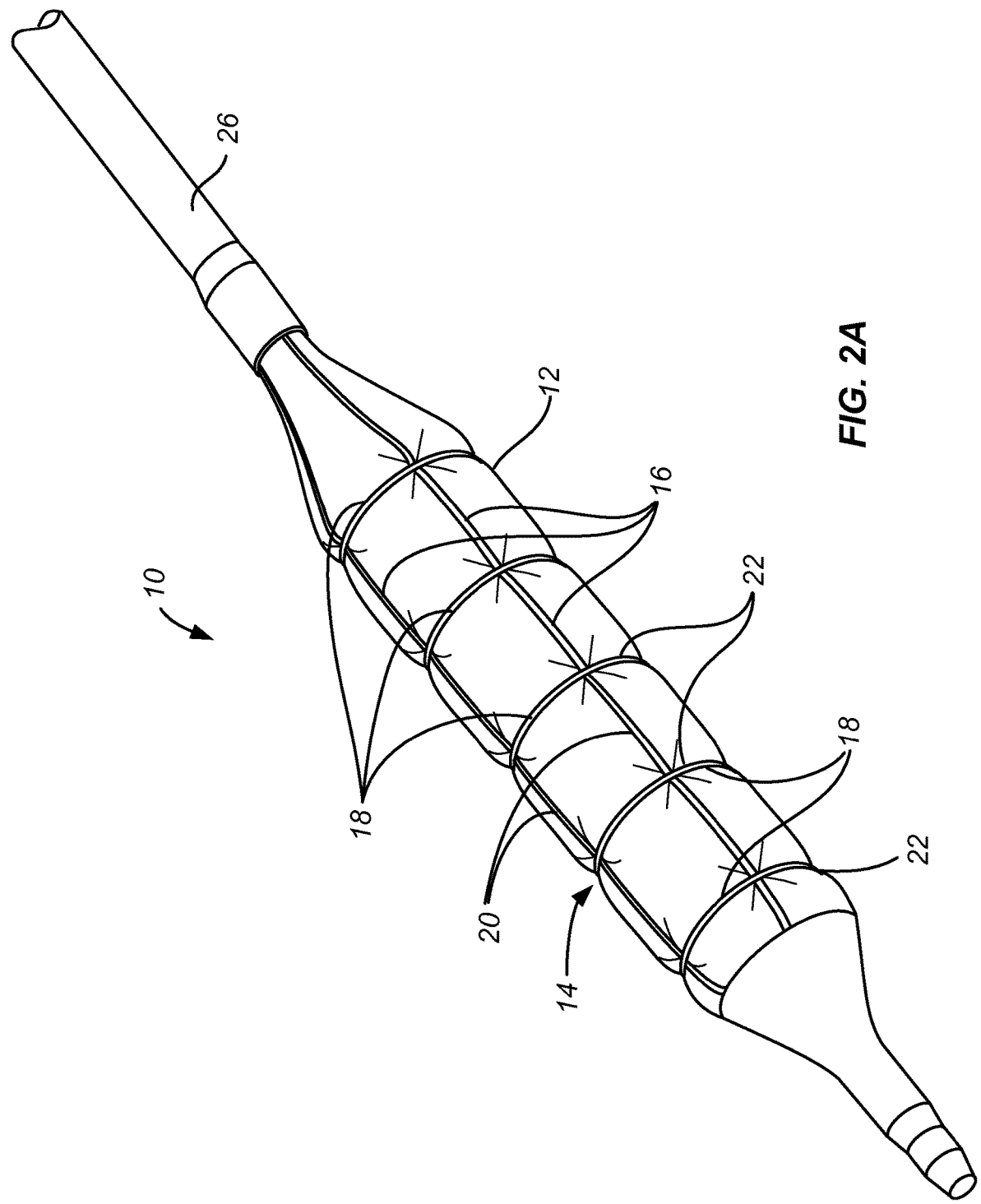
Figure 6A:
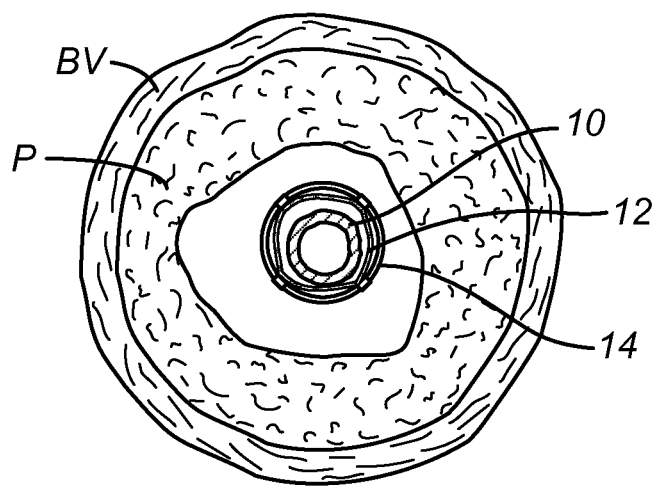
FIGS. 6A to 6C show a cross-section of the dilatation device in this invention during three stages of inflation with the balloon unwrapping within the constraining device.

Referring now to FIGS. 2A, 2B1 and 2B2, an exemplary constraining structure 14 constructed in accordance with the principles of the present invention comprises a plurality of axial struts 16 and axially spaced-apart radially expandable rings 18. When the balloon 12 and the catheter 10 is in its non-inflated state (as illustrated in FIG. 2B1), the balloon is folded with a number of overlapping lobes, as best seen in FIG. 6A (discussed below). The constraining structure 14 has a generally cylindrical geometry with a diameter just large enough to cover the deflated balloon 12.

As the balloon 12 is inflated, as illustrated in FIGS. 2A and 2B2, the radially expandable rings 18 expand in response to the force of the balloon. The rings will be structured, however, so that they reach a maximum diameter beyond which they will no longer radially expand regardless of the continued inflation or expansion of the balloon. As the axial struts 16 are attached or otherwise coupled to the radially expandable rings 18, the radially outward travel of the struts is also limited to a distance defined by the maximum diameter of the rings. Thus, as the balloon will have a fully inflated diameter which is larger than that of the maximum diameter of the radially expandable rings 18, when the balloon is fully inflated a plurality of axial and circumferential channels 20 and 22, respectively, will be formed in the balloon surface. A plurality of protruding regions 24 (as seen in FIG. 2B2) are defined in the openings or in interstices between the adjacent axial struts 16 and radially expandable rings 18. It is these protruding regions 24 which provide the benefits of the present invention as described above.

The axial struts 16 and radially expandable rings 18 of the constraining structure 14 are illustrated as simple straight beams or elements, it will be appreciated that they need to have some elasticity or stretchability in order to accommodate the radial expansion of the balloon and the radial increase in size of the rings. While the axial struts 14 need only be flexible since they can be free to slide along the catheter shaft 26 at either or both of the proximal and distal ends, the rings 18 must have the ability to elongate in the circumferential dimension as the balloon increases in diameter, although the rings will have a maximum diameter beyond which they will not expand, as discussed above. Most simply, the axial struts 16 and/or the radial expansion rings 18 may be formed from an elastic material which is capable of elongating under a tensile force, such as an elastomeric polymer, a coil spring, or the like. If such materials and/or structures are used with the radially expandable rings, however, there must also be a separate non-distensible or non-stretchable component which provides for the radial expansion limit.

Figure 3A:
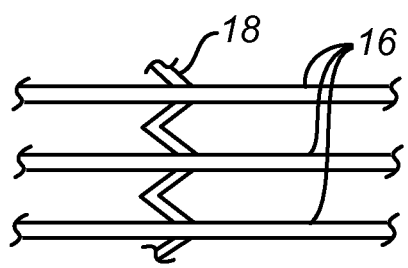
FIGS. 3A and 3B illustrate a first exemplary ring structure where the ring segments between adjacent axial struts are formed in a zig-zag pattern.
Figure 3B:
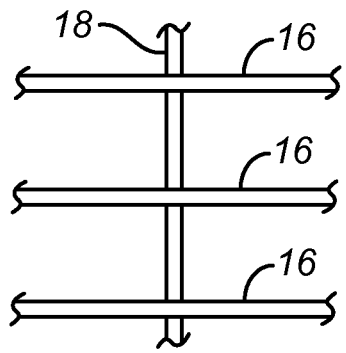
Figure 4A:
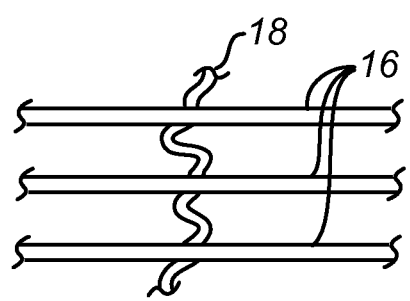
FIGS. 4A and 4B illustrate a first exemplary ring structure where the ring segments between adjacent axial struts are formed in a S-shaped pattern.
Figure 4B:
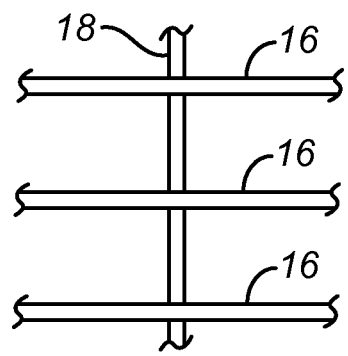
Figure 5A:
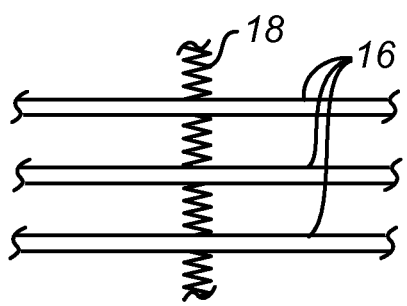
FIGS. 5A and 5B illustrate a first exemplary ring structure where the ring segments between adjacent axial struts are formed as a coil spring.
Figure 5B:
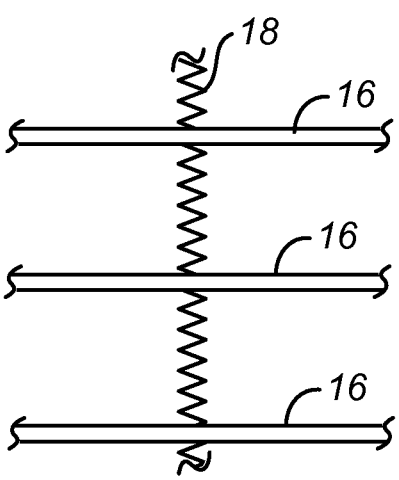

Alternatively, the axial struts 16 and/or the radially expansible rings 18 may be formed from a generally non-stretchable material, typically a metal such as a nickel-titanium alloy as noted above, and be provided with features or patterns which allow for elongation under a tensile force. For example, as illustrated in FIGS. 3A and 3B, the radially expandable rings 18 could be formed in a zig-zag pattern so that they can elongate from a shortened configuration, as shown in FIG. 3A, to a fully elongated configuration, as shown in FIG. 3B. Although not illustrated, it will be appreciated that the axial struts could employ the same geometric features allowing for axial elongation. Shown in FIGS. 4A and 4B, the rings 18 could be provided with S-shaped or serpentine structures which allow for elongation from a shortened configuration (FIG. 4A) to a fully elongated configuration (FIG. 4B) corresponding to the fully expanded diameter configuration shown in FIGS. 2A and 2B2. Alternatively, the rings 18 could be provided with a coil configuration, as shown in FIGS. 5A and 5B, where the coil will assume a shortened configuration when the ring is at its minimum diameter, as shown in FIG. 5A, and will stretch to accommodate a fully expanded configuration, as shown in FIG. 5B. The coil springs, however, like the elastic polymer embodiments described above will in most instances require a separate element or component to prevent expansion beyond the desired maximum limit.

Figure 6B:
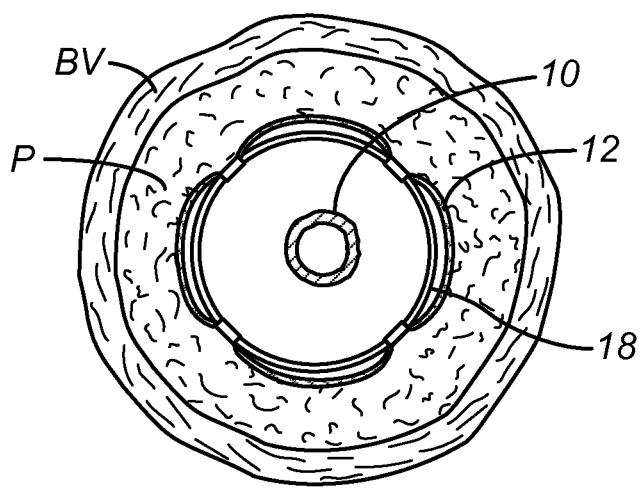
Figure 6C:
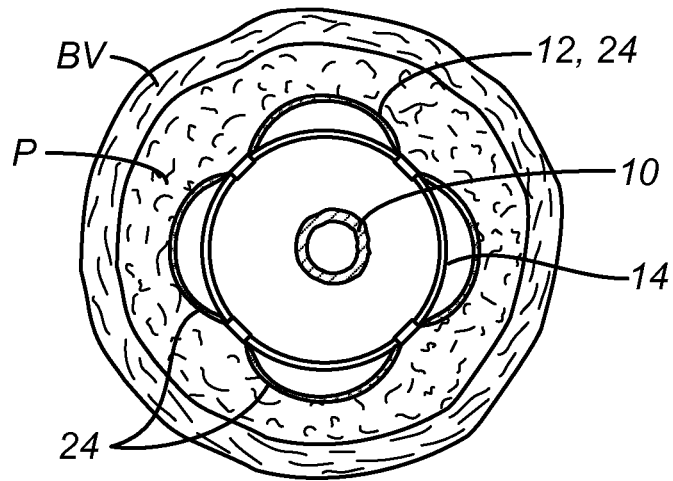

Referring now to FIGS. 6A through 6C, the catheter 10 carrying the balloon 12 and constraining structure 14 is introduced to a region of plaque P and a blood vessel BV in a generally conventional manner. Once the balloon 12 and constraining structure 14 are at the target location, the balloon is inflated, causing the constraining structure 14 to radially expand until it reaches a maximum diameter, as shown in FIG. 6B. Once it has reached its maximum diameter, the constraining structure 14 will no longer expand, but portions of the balloon 12 which are located in the open regions between adjacent axial struts and radially expandable rings will continue to expand until reaching their maximum expansion, as shown in FIG. 6C, where the fully formed protruding regions 24 are present. As the balloon 12 will typically be formed from a non-distensible material, as noted above, once the maximum balloon size has been reached further balloon inflation will not significantly increase the balloon size.

Figure 7A:
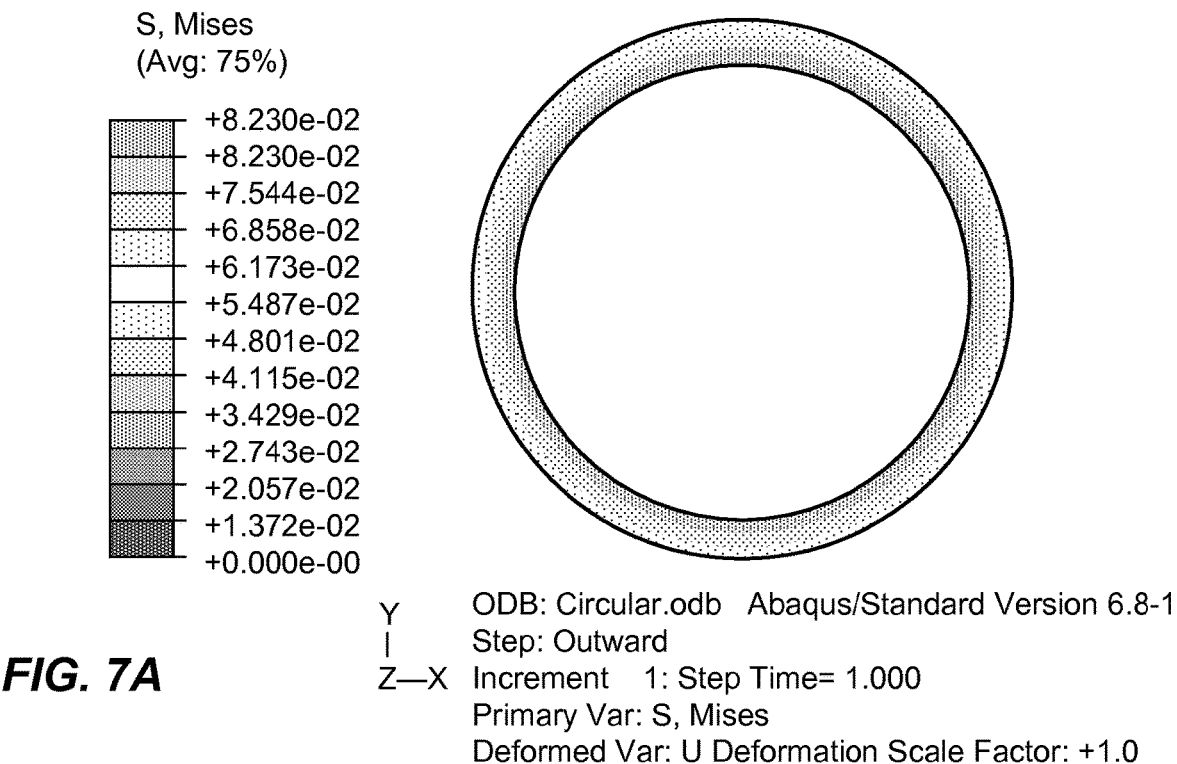
FIGS. 7A and 7B show finite element analyses of the vessel trauma of a conventional balloon and the device described in this invention.
Figure 7B:
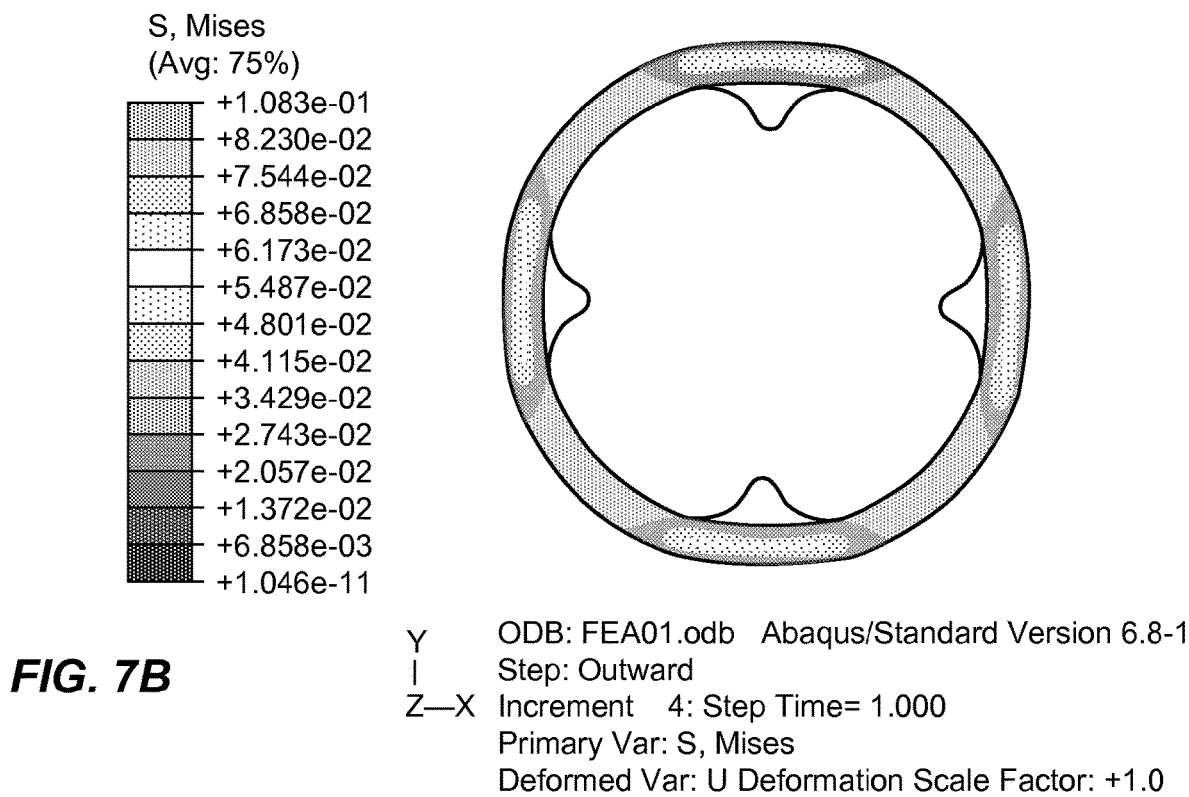

FIGS. 7A and 7B show finite element analyses of the forces applied on the vessel wall comparing a conventional balloon (FIG. 7A) with the device of the present invention (FIG. 7B). The conventional balloon displays uniform high strains in contrast to the balloon of this invention which displays stretching in the areas where the tissue is free from contact with the balloon. The uniform balloon pressure is replaced with an alternating pressure pattern that reduces vessel trauma.

The present invention can be utilized to deliver various agents or active substances particularly (but not limited to) those suitable for treating vascular and other luminal conditions such as antiproliferative and antimitotic agents (such as paclitaxel and sirolimus) other substances can include antibiotics, antiplatelet agents hormones and more.

The active substance can be placed in various designs or techniques such as directly coated on the balloon surface, the CS or both. It can be embedded in a matrix/carrier placed on the balloon or the CS or both. The combination of low trauma dilatation with release of active agent can be superior to drug eluting stents for some portions of the population by minimizing the need for a permanent implant yet providing good long term results.

In one embodiment the balloon surface is coated with drug. Upon balloon inflation, the protruding regions formed in the balloon external surface coated with drug engage the vessel wall and compress the drug into the wall to facilitate efficient drug delivery to the treated site.

Drug delivery can be facilitated using many different design methods including but not limited to coating the balloon, coating the CS structure or both. Coating with a drug directly or using a carrier in a form of a matrix or microcapsules.

While the above is a complete description of the preferred embodiment of the invention, various alternatives, modifications, additions and substitutions are possible without departing from the scope thereof, which is defined by the claims.

What is claimed is:

1. A balloon catheter comprising:
   a catheter shaft;
   a balloon on the catheter shaft; and
   a constraining structure disposed over the balloon, the constraining structure fixedly attached to the catheter shaft distal of the balloon and/or proximal of the balloon to prevent detachment of the constraining structure from the catheter shaft, the constraining structure comprising a plurality of openings;
   wherein the constraining structure is configured to transition between an unexpanded configuration and an expanded configuration;
   wherein inflation of the balloon expands the constraining structure to the expanded configuration with a plurality of isolated balloon regions protruding from the plurality of openings, the plurality of isolated balloon regions configured to contact a wall of a blood vessel with the constraining structure displaced from the wall of the blood vessel.

2. The balloon catheter of claim 1, wherein the constraining structure is fixedly attached to the catheter shaft distal of the balloon and proximal of the balloon.

3. The balloon catheter of claim 1, wherein, prior to inflation of the balloon, the balloon is folded beneath the constraining structure.

4. The balloon catheter of claim 1, wherein the balloon is coated with a drug.

5. The balloon catheter of claim 1, wherein the constraining structure is coated with a drug.

6. The balloon catheter of claim 1, wherein the plurality of isolated balloon regions are uniformly distributed over a surface of the balloon.

7. The balloon catheter of claim 1, wherein the constraining structure comprises a polymer material.

8. The balloon catheter of claim 1, wherein the constraining structure comprises an elastic material.

9. The balloon catheter of claim 1, wherein the balloon comprises a semi-compliant material.

10. The balloon catheter of claim 1, wherein the plurality of isolated balloon regions are diamond shaped.

11. A balloon catheter comprising:
   a catheter shaft;
   a balloon on the catheter shaft; and
   a constraining structure disposed over the balloon, the constraining structure fixedly attached to the catheter shaft distal of the balloon and/or proximal of the balloon to prevent detachment of the constraining structure from the catheter shaft;
   wherein inflation of the balloon expands the constraining structure to create a plurality of isolated balloon regions separated by a plurality of intersecting channels formed by the constraining structure;
   wherein the plurality of isolated balloon regions are configured to contact a wall of a blood vessel with the constraining structure displaced from the wall of the blood vessel.

12. The balloon catheter of claim 11, wherein the plurality of intersecting channels comprise two or more helical channels.

13. The balloon catheter of claim 11, wherein the plurality of intersecting channels comprise a plurality of axially oriented channels.

14. The balloon catheter of claim 11, wherein the plurality of intersecting channels comprise a plurality of circumferentially oriented channels.

15. The balloon catheter of claim 11, wherein the plurality of intersecting channels comprise a plurality of axially-oriented channels intersecting a plurality of circumferentially oriented channels.

16. The balloon catheter of claim 11, wherein at least some of the plurality of intersecting channels intersect to form an angle between 75 degrees and 105 degrees, inclusive.

17. The balloon catheter of claim 11, wherein, prior to inflation of the balloon, the balloon is folded beneath the constraining structure.

18. The balloon catheter of claim 11, wherein the balloon is coated with a drug.

19. The balloon catheter of claim 11, wherein the constraining structure is coated with a drug.

20. The balloon catheter of claim 11, wherein the balloon comprises a semi-compliant material.

* * * * *